(12) United States Patent
Zirps et al.

(10) Patent No.: US 7,204,804 B2
(45) Date of Patent: Apr. 17, 2007

(54) ENDOSCOPIC ACCESSORY MOUNTING ADAPTOR

(75) Inventors: Christopher T. Zirps, Sharon, MA (US); Timothy R. Membrino, Acton, MA (US); Scott Reed, Monroe, CT (US); Eric Mears, South Bristol, ME (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/656,557

(22) Filed: Sep. 5, 2003

(65) Prior Publication Data

US 2004/0215058 A1 Oct. 28, 2004

Related U.S. Application Data

(60) Provisional application No. 60/408,750, filed on Sep. 6, 2002.

(51) Int. Cl.
*A61B 1/00* (2006.01)

(52) U.S. Cl. .................. 600/127; 600/129; 600/104

(58) Field of Classification Search ............. 600/127, 600/104, 129, 121, 123
See application file for complete search history.

(56) References Cited

U.S. PATENT DOCUMENTS

| 4,226,239 A | 10/1980 | Polk et al. |
| 4,230,116 A | 10/1980 | Watson |
| 4,735,194 A | 4/1988 | Stiegmann |
| 4,788,966 A | 12/1988 | Yoon |
| 5,201,908 A | 4/1993 | Jones |
| 5,259,366 A | 11/1993 | Reydel et al. |
| 5,275,151 A | 1/1994 | Shockey et al. |
| D344,334 S | 2/1994 | Dulebohn et al. |
| 5,325,746 A | 7/1994 | Anderson |
| 5,356,416 A | 10/1994 | Chu et al. |
| 5,382,254 A | 1/1995 | McGarry et al. |
| 5,383,875 A | 1/1995 | Bays et al. |
| 5,409,478 A | 4/1995 | Gerry et al. |
| 5,447,148 A | 9/1995 | Oneda |
| 5,470,328 A | 11/1995 | Furnish et al. |
| 5,498,256 A | 3/1996 | Furnish |
| 5,503,616 A | 4/1996 | Jones |
| 5,507,797 A | 4/1996 | Suzuki et al. |
| 5,569,268 A | 10/1996 | Hosoda |
| 5,601,568 A | 2/1997 | Chevillon et al. |

(Continued)

OTHER PUBLICATIONS

U.S. Appl. No. 10/656,083, filed Sep. 5, 2003, Zirps et al.

(Continued)

*Primary Examiner*—Beverly M. Flanagan
(74) *Attorney, Agent, or Firm*—Kirkpatrick & Lockhart Nicholson Graham LLP

(57) ABSTRACT

The present invention relates to a mounting adapter for releasably securing accessories, tools, or their medical instruments to the distal end of an endoscope. The adapter is compatible with endoscopic accessories that have a cylindrical mounting surface, which becomes positioned over a length of the distal end of an endoscope. The adaptor is preferably provided in two components to support both ends of a cylindrical accessory on the endoscope surface. The adapter is configured to hold the accessory on the endoscope shaft by frictional engagement and is configured to maintain the accessory concentric with the shaft along its length. The adapter also is configured to mount an accessory to a wide range of commercially available endoscope diameters.

14 Claims, 7 Drawing Sheets

U.S. PATENT DOCUMENTS

| | | |
|---|---|---|
| D378,611 S | 3/1997 | Croley |
| 5,624,431 A | 4/1997 | Gerry et al. |
| 5,643,175 A | 7/1997 | Adair |
| D383,539 S | 9/1997 | Croley |
| 5,662,588 A | 9/1997 | Iida |
| D385,350 S | 10/1997 | Furnish |
| 5,690,645 A | 11/1997 | Van Erp |
| 5,725,536 A | 3/1998 | Oberlin et al. |
| 5,735,793 A | 4/1998 | Takahashi et al. |
| 5,788,715 A | 8/1998 | Watson et al. |
| 5,888,191 A | 3/1999 | Akiba |
| 5,993,384 A | 11/1999 | Lunsford et al. |
| 6,059,719 A | 5/2000 | Yamamoto et al. |
| 6,071,233 A * | 6/2000 | Ishikawa et al. ............ 600/104 |
| 6,149,659 A | 11/2000 | Ahmed |
| 6,306,081 B1 * | 10/2001 | Ishikawa et al. ............ 600/127 |
| 6,340,344 B1 | 1/2002 | Christopher |
| D459,474 S | 6/2002 | Bratt et al. |
| 6,576,005 B1 | 6/2003 | Geitz |
| D480,807 S | 10/2003 | Yardan et al. |
| 6,685,713 B1 | 2/2004 | Ahmed |
| 6,699,180 B2 * | 3/2004 | Kobayashi .................. 600/127 |
| 2001/0027312 A1 | 10/2001 | Bacher et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0208209 A1 | 11/2003 | Gambale et al. |
| 2004/0034371 A1 | 2/2004 | Lehman et al. |

OTHER PUBLICATIONS

U.S. Appl. No. 10/656,085, filed Sep. 5, 2003, Zirps et al.
U.S. Appl. No. 10/656,557, filed Sep. 5, 2003, Zirps et al.
U.S. Appl. No. 10/658,135, filed Sep. 8, 2003, Aznoian et al.
U.S. Appl. No. 10/658,619, filed Sep. 8, 2003, Gambale et al.
U.S. Appl. No. 10/847,190, filed May 17, 2004, Gambale et al.
U.S. Appl. No. 10/847,190, filed May 2004, Gambale et al.
U.S. Appl. No. 10/658,619, filed Sep. 2003, Gambale et al.
U.S. Appl. No. 10/658,135, filed Sep. 2003, Aznoian et al.
U.S. Appl. No. 10/656,557, filed Sep. 2003, Zirps et al.
U.S. Appl. No. 10/656,085, filed Sep. 2003, Zirps et al.
U.S. Appl. No. 10/656,083, filed Sep. 2003, Zirps et al.

* cited by examiner

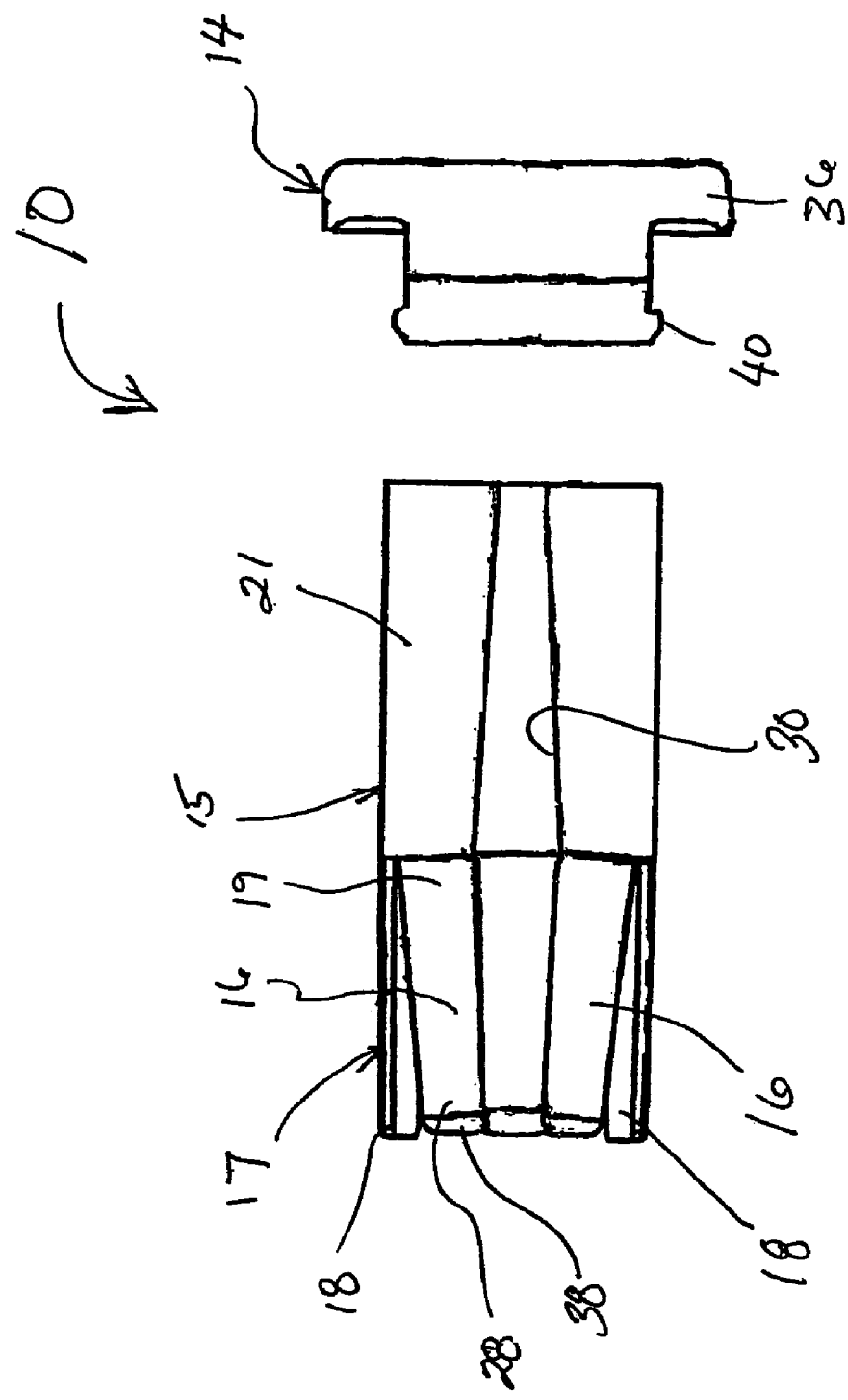

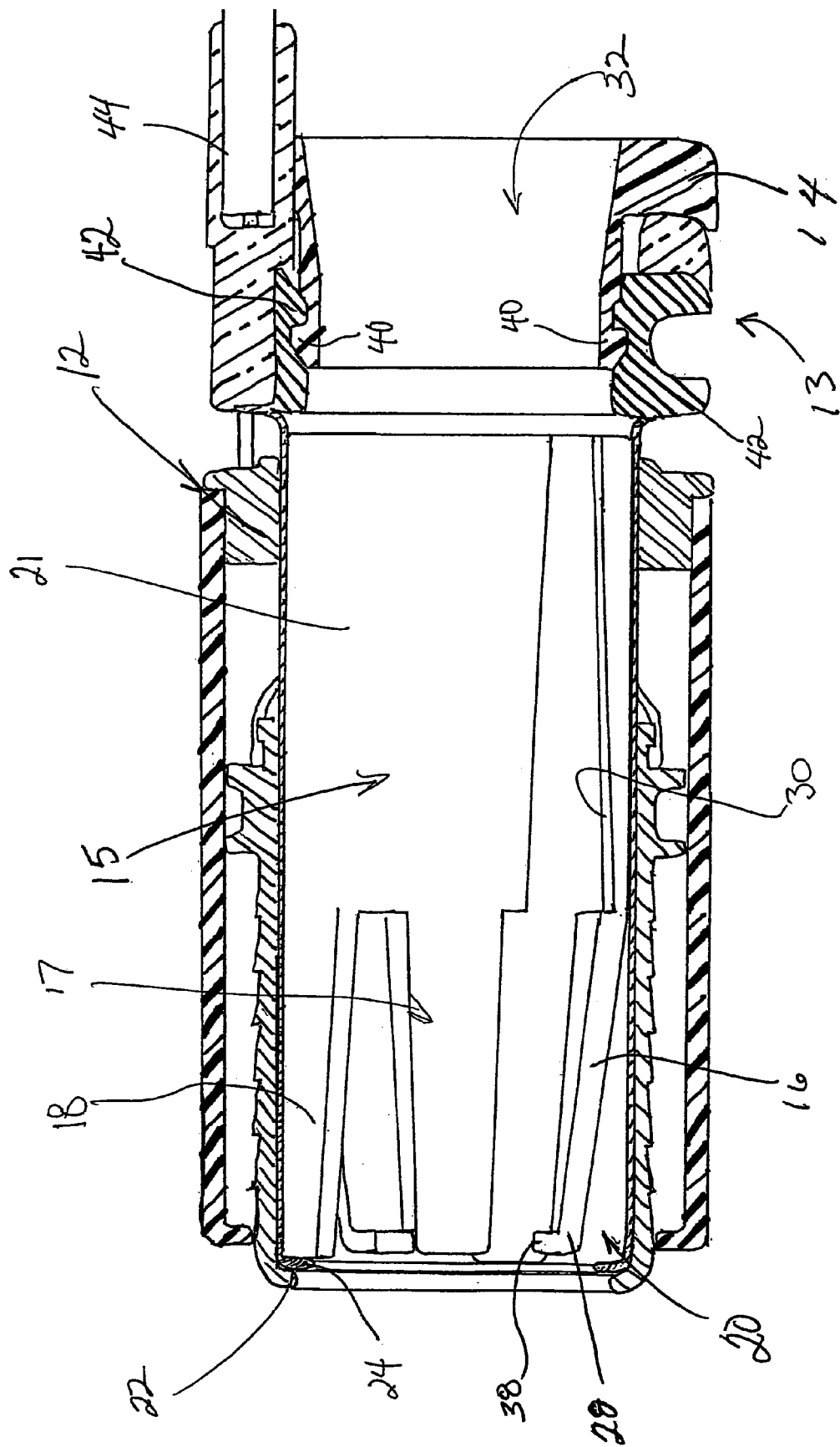

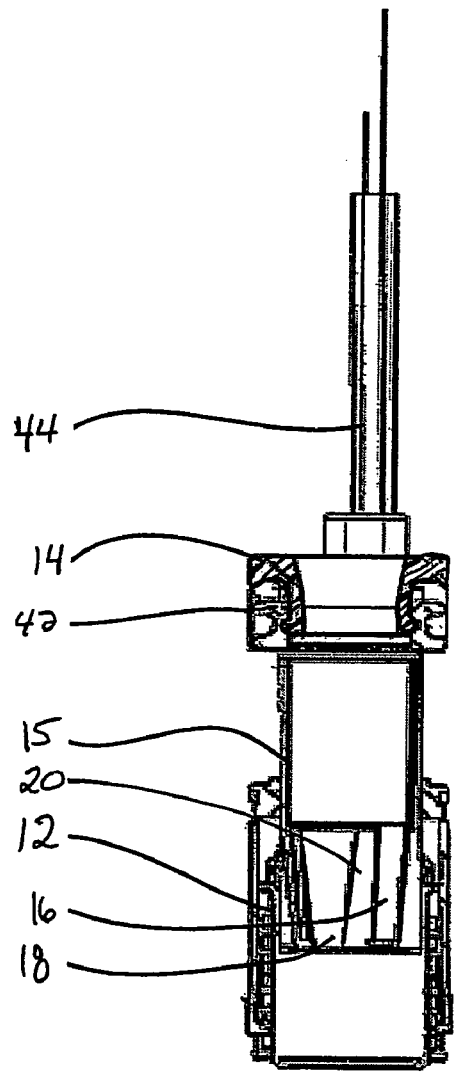
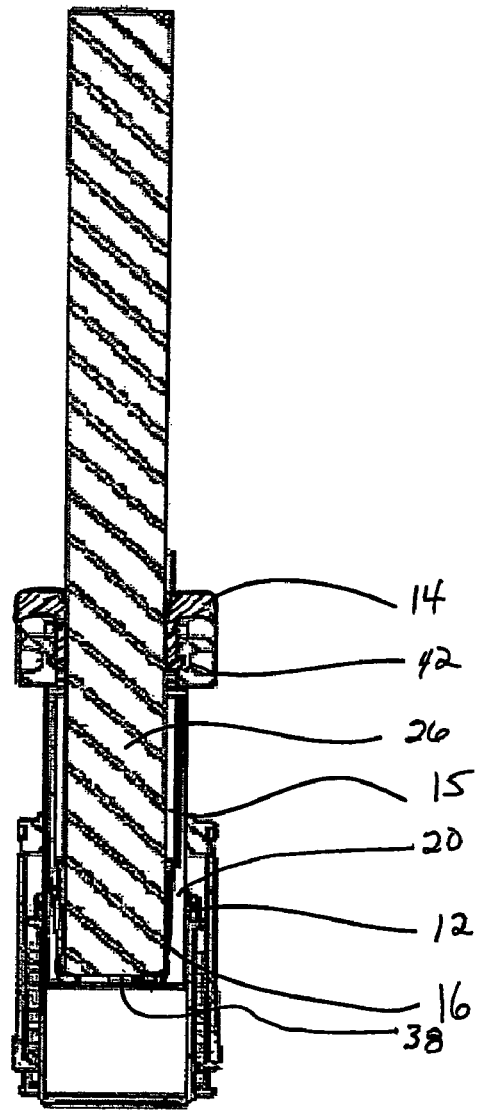
FIG. 4 A     FIG. 4 B

ENDOSCOPIC ACCESSORY MOUNTING ADAPTOR

This application claims the benefit of Provisional Application No. 60/408,750, filed Sep. 6, 2002.

FIELD OF THE INVENTION

The present invention relates to medical instrument accessories for endoscopes and methods for their use. In particular, the invention relates to devices and methods for mounting an endoscopic accessory device to an endoscope.

BACKGROUND OF THE INVENTION

Endoscopes are elongate instruments navigable through natural body lumens of a patient for the purpose of remotely evaluating and treating a variety of ailments. Endoscopes have viewing capability provided by fiber optic elements that transmit images along their length to the medical care provider. Endoscopes may specifically configured in length, diameter, flexibility and lumen configuration to navigate specific treatment areas in the body. Such specifically configured endoscopes may be known as a laparoscope, duodenoscope, colonoscope, sigmoidoscope, bronchoscope and urethroscope among others. In combination with remote viewing capability, endoscopes are frequently configured to provide a working channel through which shaft mounted tools and medical instruments may be navigated and remotely operated. Additionally, the endoscope shaft itself may carry a medical instrument for remotely performing a procedure at an internal treatment site, while permitting direct visualization of the site through the endoscope.

The present invention addresses the problem of making an endoscopic accessory readily joinable to a range of endoscope sizes that are commercially available from a variety of manufacturers. Endoscopic accessories may include such instruments as forceps, band ligators or suturing devices, among others. The devices generally mount to at least a small portion of the outside surface of an endoscope shaft. A common mechanism for attachment of the accessory to the endoscope is by frictional engagement. The accessory is provided with a proximal portion having a circular or semicircular cross-section capable of fitting over the cylindrical shaft of the endoscope. The diameter defined by the proximal end of the accessory is sized to provide a frictional engagement with the endoscope shaft surface. An elastic gasket or ring may additionally be inserted between the endoscope shaft and the accessory to promote frictional engagement. However, because there is no standardized endoscope size and different endoscope manufacturers make endoscopes of different diameters, ensuring that the selected endoscope accessory will be sized appropriately to frictionally engage an endoscope can be problematic. This is especially so considering that the selected endoscope accessory may be manufactured by a different supplier than that of the endoscope. The present invention endeavors to provide a mounting adapter that will be usable with a variety of endoscopic accessories to provide a secure mounting to a variety of endoscope shaft sizes.

Another potential problem with current endoscopic accessory mounting techniques is insuring a proper support and alignment of the accessory in relation to the endoscope shaft. In particular, an endoscopic accessory having a cylindrical receptacle that mounts along a length of the distal end of the endoscope shaft may not be adequately supported by a narrow circular area of frictional engagement at one end of the cylindrical receptacle. For example, if a cylindrical accessory is engaged with the endoscope shaft only by a single elastic ring at the proximal end of the device, the accessory may become misaligned at its distal end so that it is not concentric with the endoscope shaft. The accessory is then not aligned with the longitudinal axis of the endoscope, which can lead to mispositioning of the accessory relative to the intended treatment site. The present invention endeavors to provide an adapter that centers the accessory on the endoscope shaft maintaining it concentric along its length so that it is substantially aligned with the longitudinal axis of the endoscope.

SUMMARY OF THE INVENTION

The present invention provides a mounting adapter for an endoscopic accessory that is compatible with a wide range of endoscope sizes to provide a frictional engagement that secures the accessory to the endoscope. The adapter also serves to center the accessory concentrically with the endoscope shaft. Current commercially available endoscopes are provided in various diameter sizes depending on manufacturer. The adaptor is configured to accept a range of different endoscope diameters to make endoscope accessories more universally functional with available endoscopes.

The adapter comprises a centering sleeve insertable within a tubular accessory to support its distal end on an endoscope and a separate collar insertable in the proximal end of the accessory to provide engagement with the endoscope shaft. The centering sleeve comprises resiliently radially expandable elements that engage the endoscope shaft surface and serves to absorb variances in clearance between the endoscope shaft diameter and inside diameter of the accessory. The collar may be formed from flexible, resilient material that frictionally engages both the outside surface of the endoscope shaft and the inside surface of the accessory. The centering sleeve and collar may be axially spaced apart from each other while retaining the accessory on the surface of the endoscope.

The centering sleeve may be of tubular shape to engage the inside circumference of a tubular accessory and the exterior surface of an endoscope shaft. A longitudinal slit may be formed along the length of the sleeve to provide additional radial flexibility to accept a wide range of endoscope diameters through the bore defined by the sleeve.

The collar is preferably ring shaped, having a center hole to receive the endoscope shaft. The collar is preferably formed from a flexible, elastic material to provide a limited range of flexibility in accepting different endoscope sizes through the center hole. Preferably, the collar is of the requisite size and flexibility such that the endoscope shaft fits snugly through the center hole to create a frictional engagement. To accommodate a full range of endoscope sizes equivalent to that accepted by the centering sleeve, several collars of differing sizes may be provided with the adapter and may be interchangeably used in combination with the centering sleeve to accommodate a full range of commercially available endoscope sizes. The adapter comprising the centering sleeve and several collars of differing sizes can be provided to the end user as a kit. An endoscope diameter gauge block may be provided in the kit to help the user identify the diameter of the endoscope being used. Having identified the diameter of the endoscope, the user then selects the appropriate collar to match the size of endoscope being used. The three collars may be color coded to facilitate selection of the appropriate size for a given endoscope.

It is an object of the present invention to provide an endoscopic accessory mounting adapter that readily accommodates various sizes of endoscopes.

It is another object of the invention to provide an endoscopic accessory mounting adapter that provides support at both proximal and distal engagement locations between the accessory and the endoscope to ensure proper alignment of the accessory on an endoscope.

It is another object of the invention to provide an endoscopic accessory mounting adapter comprising two components that are separately engageable with the accessory to provide a secure interface with the endoscope shaft.

It is another object of the invention to provide a method of mounting an endoscopic accessory that comprises inserting first and second components of the adapter into the accessory prior to mounting on the endoscope.

It is another object of the invention to provide an endoscopic accessory mounting adapter kit that comprises a centering sleeve and a plurality of collars of different sizes corresponding to different size ranges of endoscopes.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 1 is a side view illustration of the adaptor of the present invention;

DESCRIPTION OF THE ILLUSTRATIVE EMBODIMENTS

Figure 2B:
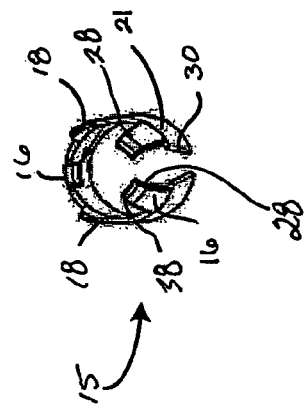
FIG. 2B is a elevational front view of the centering sleeve of the mounting adapter.
Figure 2D:
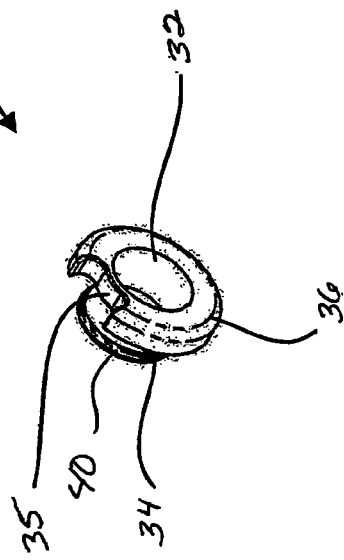
FIG. 2D is a isometric view of a collar of the mounting adapter.
Figure 2A:
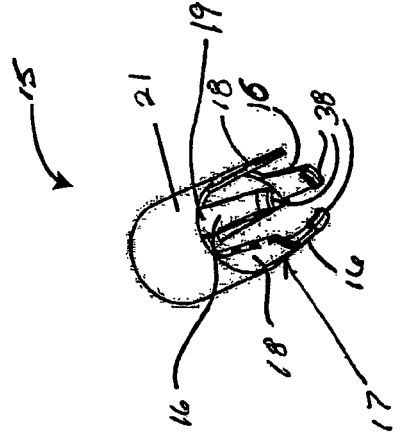
FIG. 2A is an isometric view of the centering sleeve of the mounting adapter.
Figure 2C:
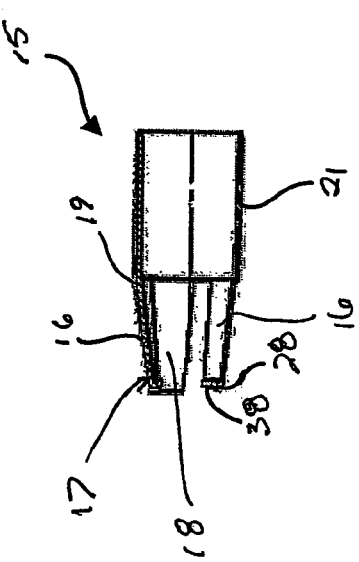
FIG. 2C is a side sectional view of the centering sleeve of the mounting adapter.

The accessory mounting adaptor 10, shown in FIG. 1, comprises two separate components that fit between the bore of an accessory and the distal end of an endoscope in order to secure the accessory to the endoscope. The two-piece adaptor 10 comprises a centering sleeve 15 having a distal end 17 formed into a plurality of resilient fingers 16 and support fingers 18 (also shown in FIGS. 2A–C) and an interchangeable collar 14 (FIG. 2D).

Figure 5:
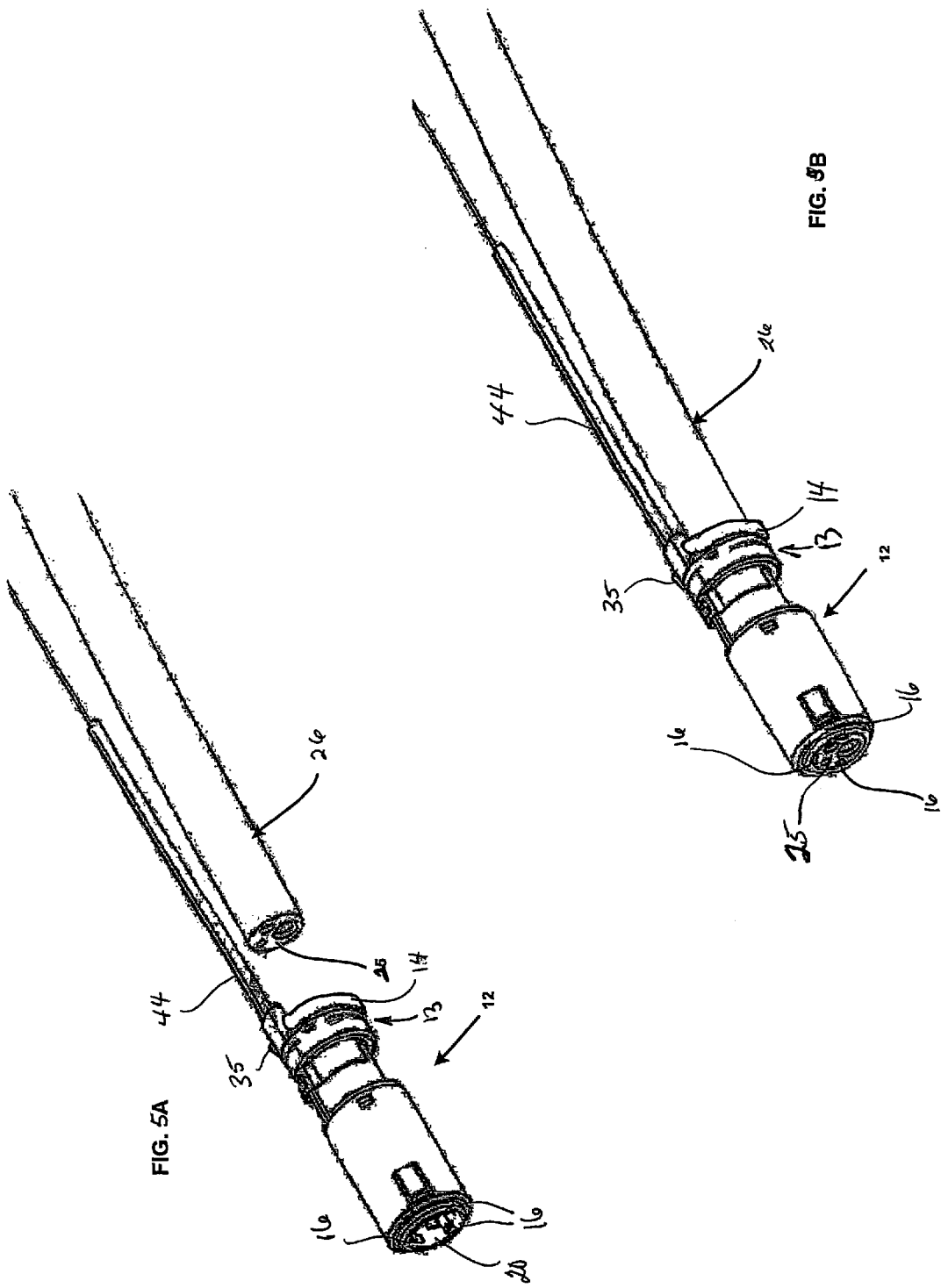
FIG. 5A is an isometric illustration of an accessory and adaptor being loaded onto the distal end of an endoscope.
FIG. 5B is an isometric illustration of an accessory and adaptor mounted onto the distal end of an endoscope.
Figure 3:
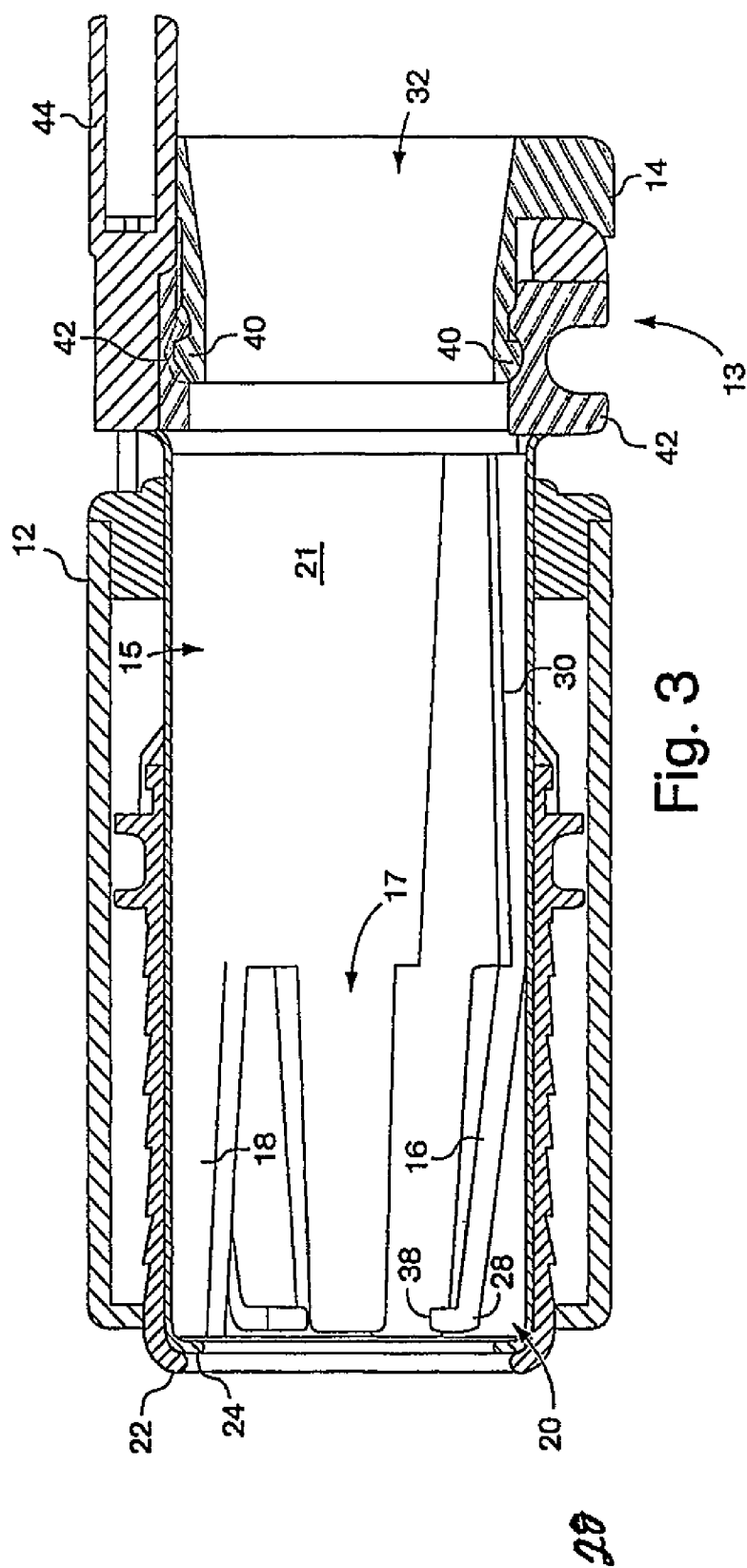
FIG. 3 is a diagrammatic sectional illustration of a mounting adapter of the present invention inserted into an endoscopic accessory.
Figure 4:
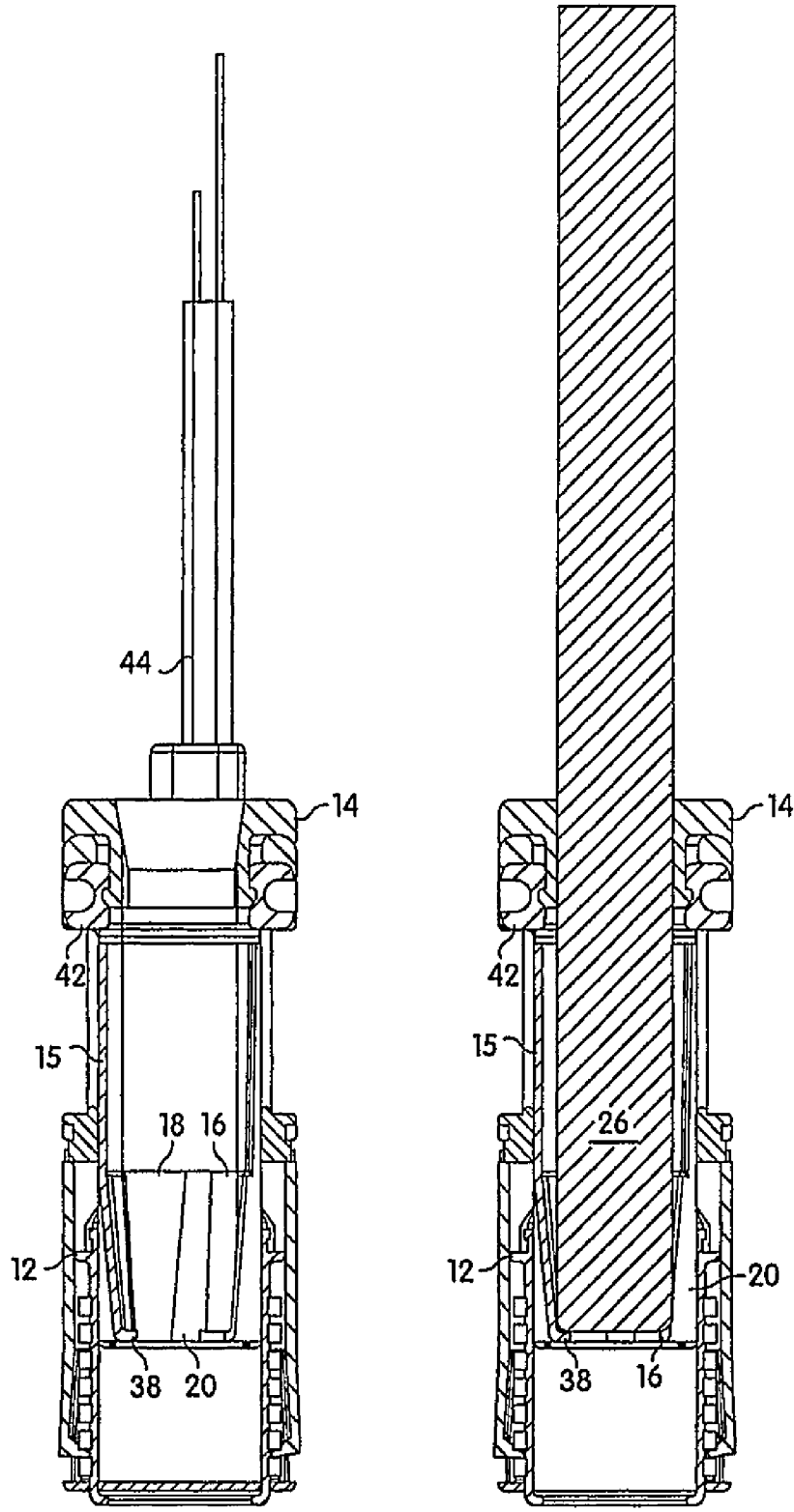
FIG. 4A is a diagrammatic sectional illustration of a mounting adapter of the present invention inserted into an endoscopic accessory.
FIG. 4B is a diagrammatic sectional illustration of a mounting adapter of the present invention inserted into an endoscopic accessory and received over an endoscope shaft.
Figure 5:
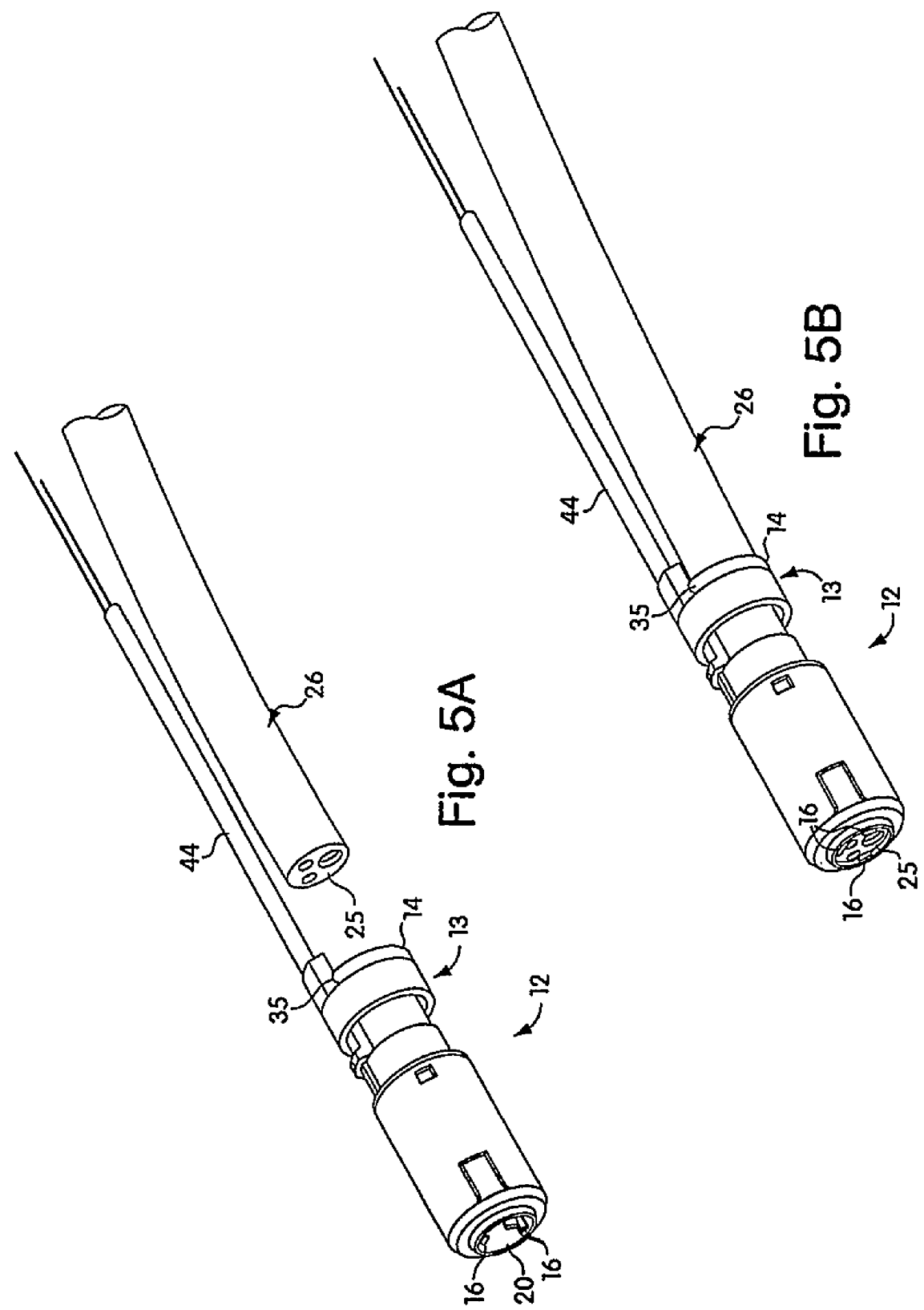
Figure 6:
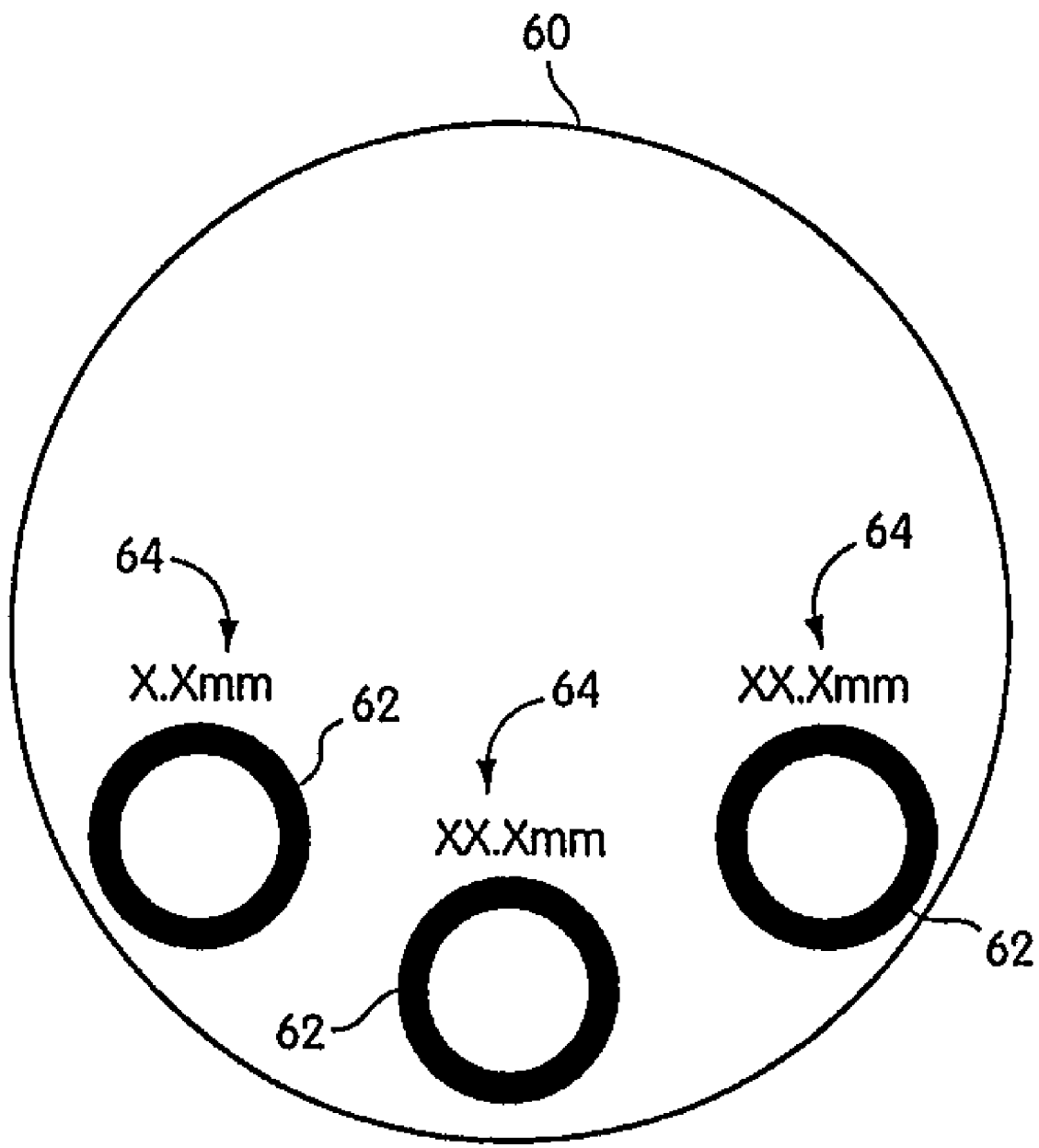
Figure 7:
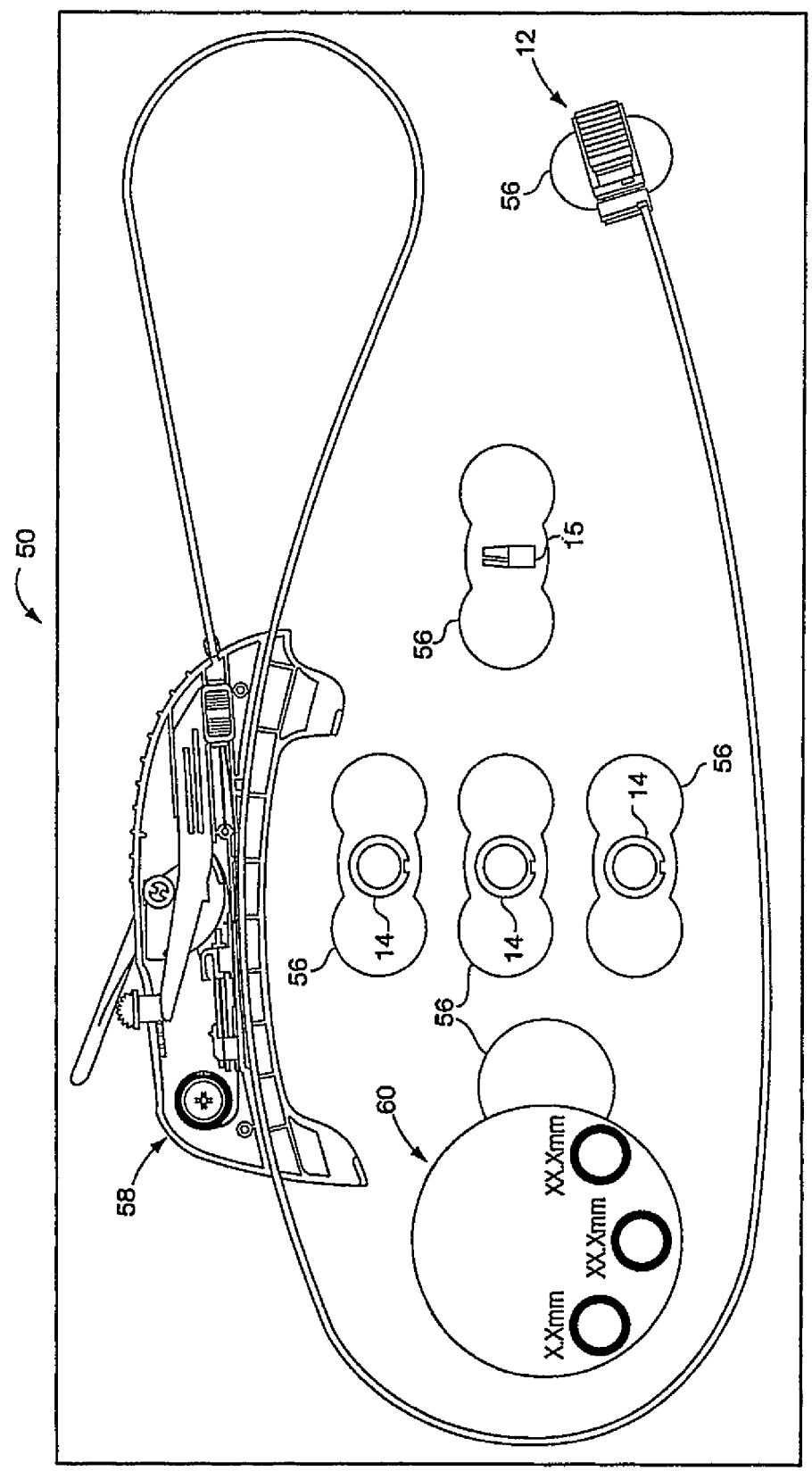

The adaptor components fit into a bore 20 of an endoscopic accessory 12, as shown in the sectional illustrations of FIGS. 3 and 4A. The components are preferably inserted into the bore 20 of the accessory prior to mounting on an endoscope 26 but alternatively may be configured to be placed on the endoscope shaft first with the accessory later being loaded over them. To assemble the adaptor with an accessory, the centering sleeve 15 first is inserted through the proximal end 13 of the bore 20 of the accessory 12, with fingers 16 and 18 pointing distally. The centering sleeve 15 is pushed to distal end 22 of the accessory bore so that support fingers 18 can engage an inner lip 24 formed around the distal edge of the bore 20, as shown as shown in FIGS. 3, 4A and 5A. The collar 14 is then fit into the proximal end of the accessory bore. Depending on the length of the accessory the centering sleeve and collar may not be in contact with each other when assembled in the bore of the accessory. As shown in the examples of FIGS. 3, 4A and 4B, the accessory is longer than the combined length of the centering sleeve and the collar, thus the collar and sleeve are not in contact when assembled inside the bore. Rather, the centering sleeve serves to position the distal end of the accessory on the scope and the collar serves to position the proximal end of the accessory.

After the centering sleeve and collar are positioned in the accessory, the distal end of the endoscope 26 may be inserted into the proximal end of the accessory, through the collar 14 and centering sleeve 15. The endoscope is advanced distally into the adaptor until the distal face of the endoscope 25 abuts inwardly projecting lips 38 on the resilient fingers 16, discussed in greater detail below.

The adaptor maintains the accessory of the device concentric with the endoscope shaft and holds it securely to the shaft by friction. It is contemplated that the adaptor could be used with any endoscope accessory that is cylindrical and that mounts over a portion of the distal end of an endoscope shaft. The adaptor components are held within the accessory 12 by friction. By way of example, for an accessory having a bore with an inside diameter of about 0.465 inch, the centering sleeve would be sized to have an outside diameter of about 0.460 inch and inside diameter of about 0.416 inch. For an accessory having a bore of a length on the order of 3.8 cm the centering sleeve may be approximately 1.125 inches in length with a proximal portion 21 measuring about 0.645 inch of that length. The centering sleeve is formed from a rigid but elastic material such as Ticona-Celecon M270 acetal copolymer, which permits the sleeve to be compressed slightly to be loaded into an accessory bore then expand to its original diameter after being released inside the bore. The expanding centering sleeve becomes engaged with the inside surface of the accessory bore. Additionally, the centering sleeve 15 may be provided with a longitudinal slot 30 along its length to provide the adaptor with additional radial flexibility in fitting different accessories and in accepting scopes of different sizes.

When the accessory 12 and loaded adaptor 10 are placed over the distal end of an endoscope 26, differences between the scope outside diameter and the accessory inside diameter are absorbed by the adaptor by virtue of the resilient fingers. The centering sleeve 15, shown in FIGS. 1–5B compensates for variations in scope diameters by the frictional engagement of several resilient fingers 16 with the endoscope shaft. The resilient fingers are coextensive with the centering sleeve proximal portion 21 at their proximal ends 19 and extend distally and radially inward so that the distal ends 28 of the fingers define a smaller diameter than that of the centering sleeve proximal portion 21. The angle of inward deflection of the fingers may be on the order of about 7 degrees from the longitudinal axis of the sleeve and accessory bore. The distal ends of the fingers 28 terminate in radially inwardly extending lips 38 that catch the distal face 25 of the endoscope when the adaptor is fully seated onto the endoscope shaft. The lips may be formed to project at an angle of about 90 degrees to the longitudinal axis of the resilient fingers. As the assembled adaptor 10 and accessory 12 are slipped onto an endoscope shaft, the resilient fingers 16 are pushed radially outward from their relaxed position to the extent necessary to accept the endoscope shaft being used. For a centering sleeve of the dimensions described above, three resilient fingers of about 0.100 to 0.200 in width, relatively equally spaced around the circumference of the centering sleeve is believed to provide adequate engagement with the endoscope shaft. However more or fewer resilient fingers may be provided to best suit the particular application.

When installed on an endoscope, the proximal portion 21 of the sleeve and fingers 16 become stressed radially outward slightly and, due to the elastic material of the centering sleeve, produce an opposing inward force on the endoscope shaft surface. The inwardly applied forces of the adaptor body and fingers provide frictional contact with the shaft to provide secure mounting and the forces provided by the equally spaced fingers maintain the adaptor and accessory concentric with the shaft.

Support fingers 18 extend distally from the centering sleeve 15 to support the distal end 22 of the accessory 12 relative to the adaptor and to provide an abutting engagement with the lip 24 of the distal end of the accessory. The support fingers are approximately the same length as the resilient fingers but may be shorter or longer than the resilient fingers to vary the position of the distal face 25 of the endoscope relative to the accessory. The support fingers extend coextensively with the proximal portion 21 of the centering sleeve, rather than tapering radially inward, to remain in contact with the inside surface of the accessory bore 20. On a centering sleeve having three equally circumferentially spaced resilient fingers 16, two support fingers, spaced apart around the circumference of the centering sleeve, is believed to provide adequate support for the accessory though a different number of support fingers may be provided.

Figure 7:
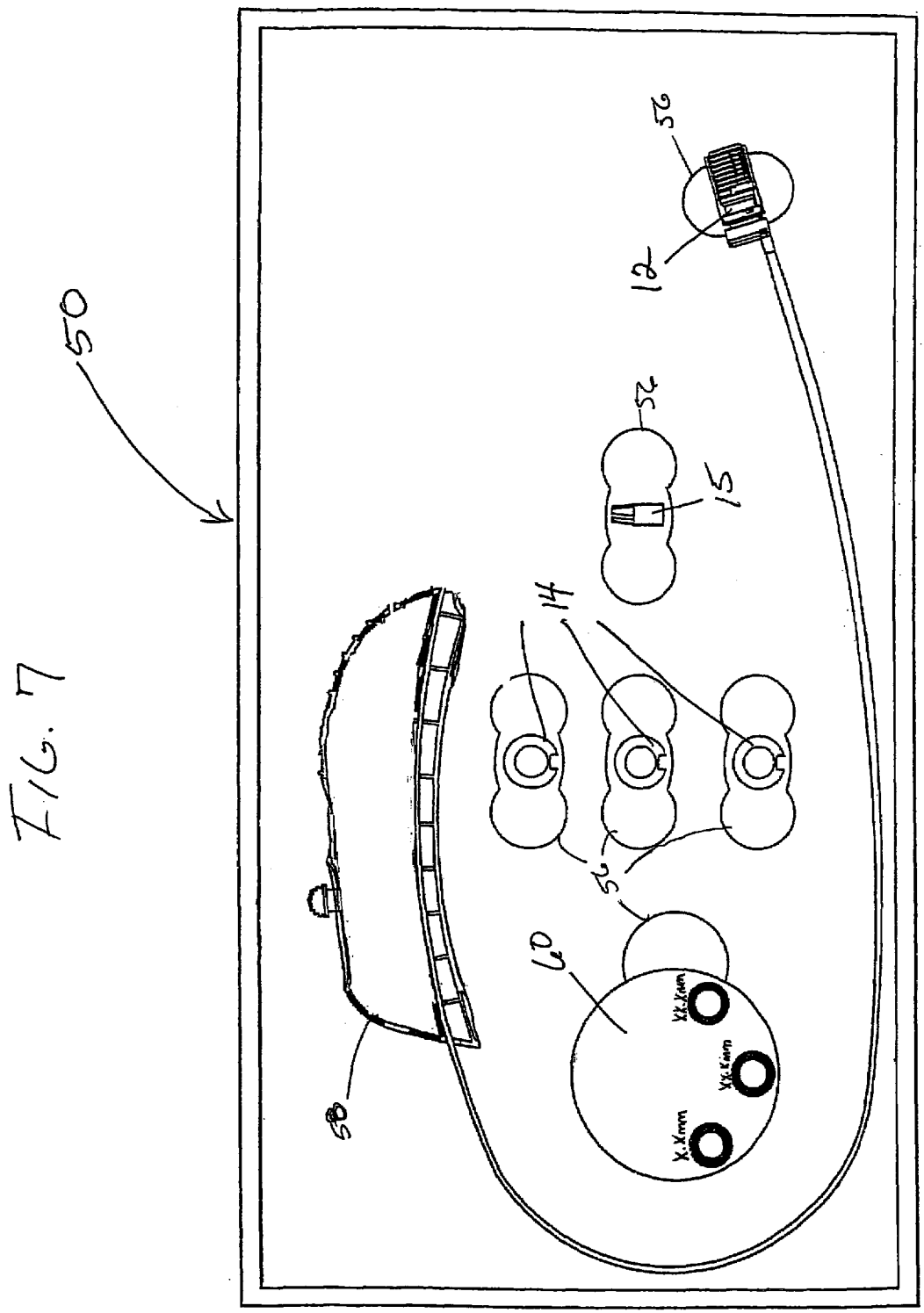
FIG. 7 is a top view of an endoscopic accessory mounting adapter kit according to the present invention.
Figure 2A:
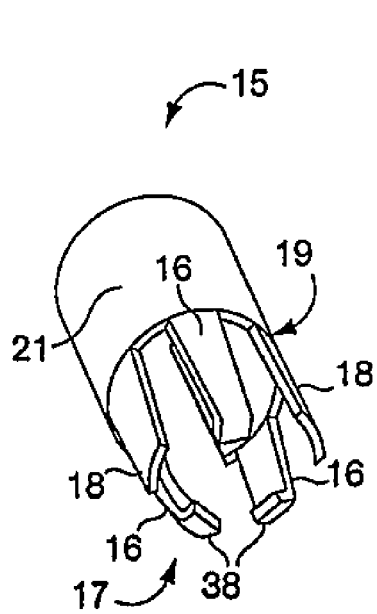
Figure 2C:
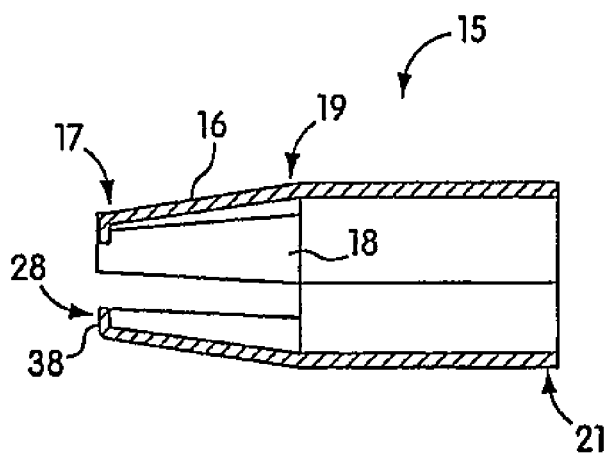
Figure 2B:
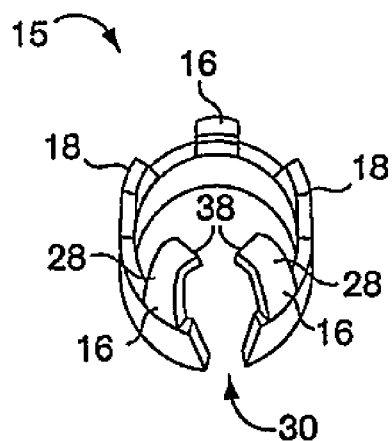
Figure 2D:
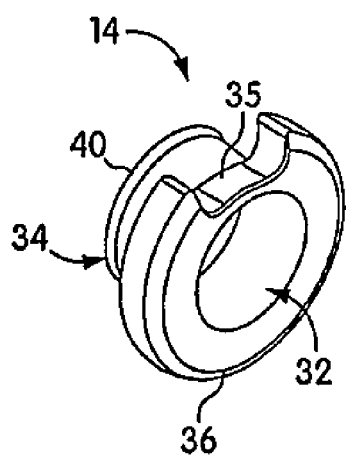

The user completes assembly of the adaptor 10 in the accessory 12 by choosing and inserting an appropriate size collar 14 for the diameter of the endoscope that will be used. The collar is formed from a flexible, pliable material that provides good frictional contact with the accessory and with the scope shaft to prevent relative movement between them. An example of a suitable material is Wacker 3003/50 LSR. A plurality of flexible collars 14 (FIG. 2D) each interchangeable with the centering sleeve 15 can be provided to the user in a kit 50 as shown in FIG. 7. Each collar has a center hole 32 with an inside diameter appropriate to fit tightly about a limited range of commercially available endoscope size ranges. For example, three collars of different center hole sizes may be provided to service a broad range of commercially available endoscope sizes. To illustrate a sample configuration: a small collar having a center hole of approximately 0.277 inch in diameter would be used with scopes ranging from 8.5 mm to 9.3 mm in diameter; a medium collar with a center hole of approximately 0.380 inch would service scopes of 9.3 mm to 10.2 mm in diameter; and a large collar with a center hole of 0.405 inch in diameter would be used to endoscopes of 10.2 mm to 10.8 mm diameter.

The collar 14 has an insert portion 34 and a flange 36 of a large diameter, greater than that of the centering sleeve 15. The collar is assembled by pushing the insert portion 34 into the proximal end of the accessory bore. An annular rib 40 projecting radially outward near the distal end of the insert portion 34 serves to catch onto the inside surface of the accessory bore 20. The rib preferably catches on a sealing ring 42 that may be provided in an accessory bore 20 by the manufacturer to provide a friction fit with an endoscope of a given size. It is noted that with the adaptor components in place within accessory 20 of accessory, a sealing ring 42 originally provided with the accessory from the manufacturer may not contact the endoscope surface directly as originally intended by the manufacturer. However if so equipped, the sealing ring 42, will engage the insert portion 34 of the adaptor collar 14 to create a suitable frictional engagement between the shaft and accessory. Additionally, if the accessory is of the type that requires a vacuum seal to maintain suction for aspirating tissue into the accessory, such as a band ligator requiring an adequate vacuum seal for aspirating varix tissue sections, the pliable collar creates a sufficient air tight seal between the accessory and endoscope surface to enable such vacuum creation.

The flange 36 is sufficiently large to become abutted against the accessory 12 when the insert portion is fully inserted into the bore 20. The flange prevents the collar from being dragged into the bore due to frictional engagement of the advancing endoscope surface with the center hole 32. A cutout 35 may be formed through a small portion of the collar flange to accommodate passage of control cables 44 that may extend longitudinally along the exterior of the endoscope 26 to operate the accessory 12.

Figure 6:
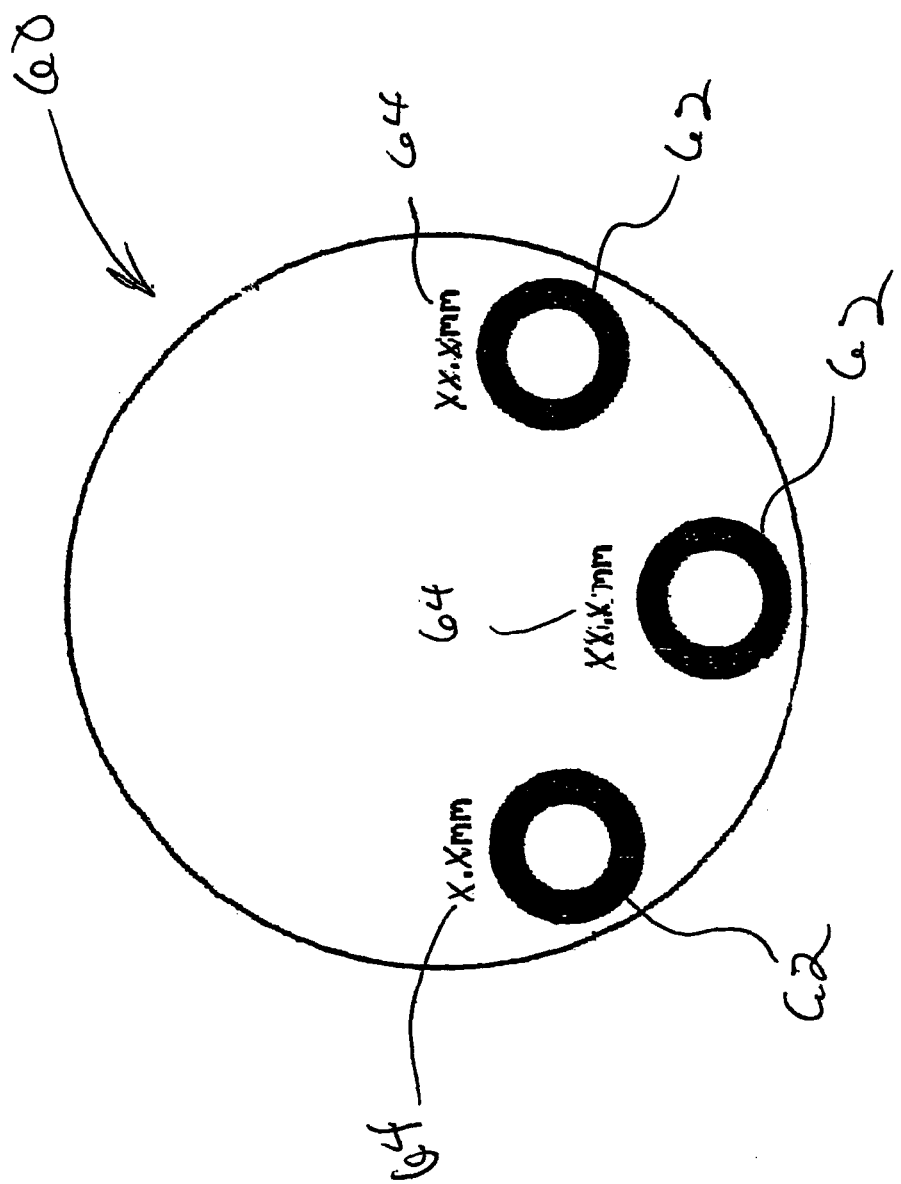
FIG. 6 is a top view of an endoscope diameter gauge block.

If the adaptor is provided in a kit form, an endoscope diameter gauge block may be provided to help the user identify the diameter of the endoscope being used. A top view of an endoscope diameter gauge block 60 is shown in FIG. 6. The gauge block may be formed from any rigid material capable of holding the dimensions of gauge hole. A plurality of gauge holes 62 may be provided, each of a greater diameter than the next, to help a user identify the diameter of the endoscope being used. The user inserts the endoscope into the holes and identifies the smallest gauge hole through which the endoscope shaft will fit. Diameter measurement markings 64 corresponding with each gauge hole will identify for the user the diameter of the hole through which the endoscope is being passed. With the diameter of the endoscope known, the user may then select the appropriate sized collar to be used with the centering sleeve in assembling the adaptor in an accessory. In addition to the diameter measurement markings, each gauge hole may be color coded to correspond to several color-coded collars in order to facilitate measurement and selection by the user.

FIG. 7 shows a kit 50 containing the components of the adaptor system. Because the adaptor comprises several components it may be most convenient to provide the adaptor as a kit to the end user. The kit should contain a centering sleeve 15 and several collars 14 to fit a range of endoscope sizes. Additionally, the kit may be provided with an endoscope diameter gauge block 60, as discussed above. The adaptor components also may be provided as a kit together with the endoscopic accessory 12. As shown in FIG. 7 the kit comprises an endoscopic accessory 12 along with its associated operation handle 58 along with the adaptor components. Each item of the kit may be retained in shaped receptacles 56 formed in a plastic tray along with other customary packaging materials.

It should be understood however, that the foregoing description of the invention is intended merely to be illustrative thereof and that other modifications, embodiments and equivalents may be apparent to those who are skilled in the art without departing from its spirit.

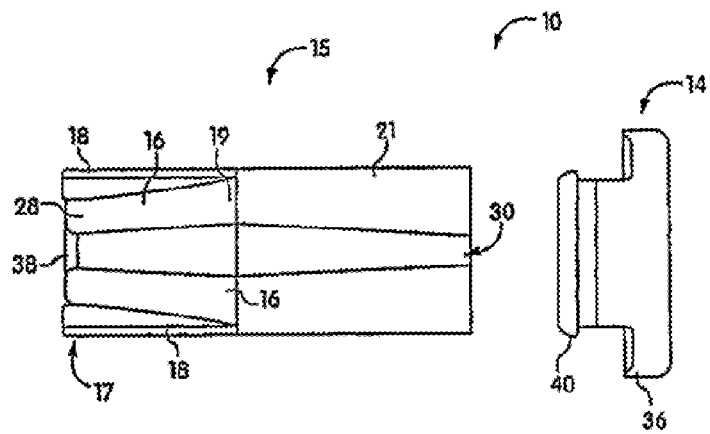

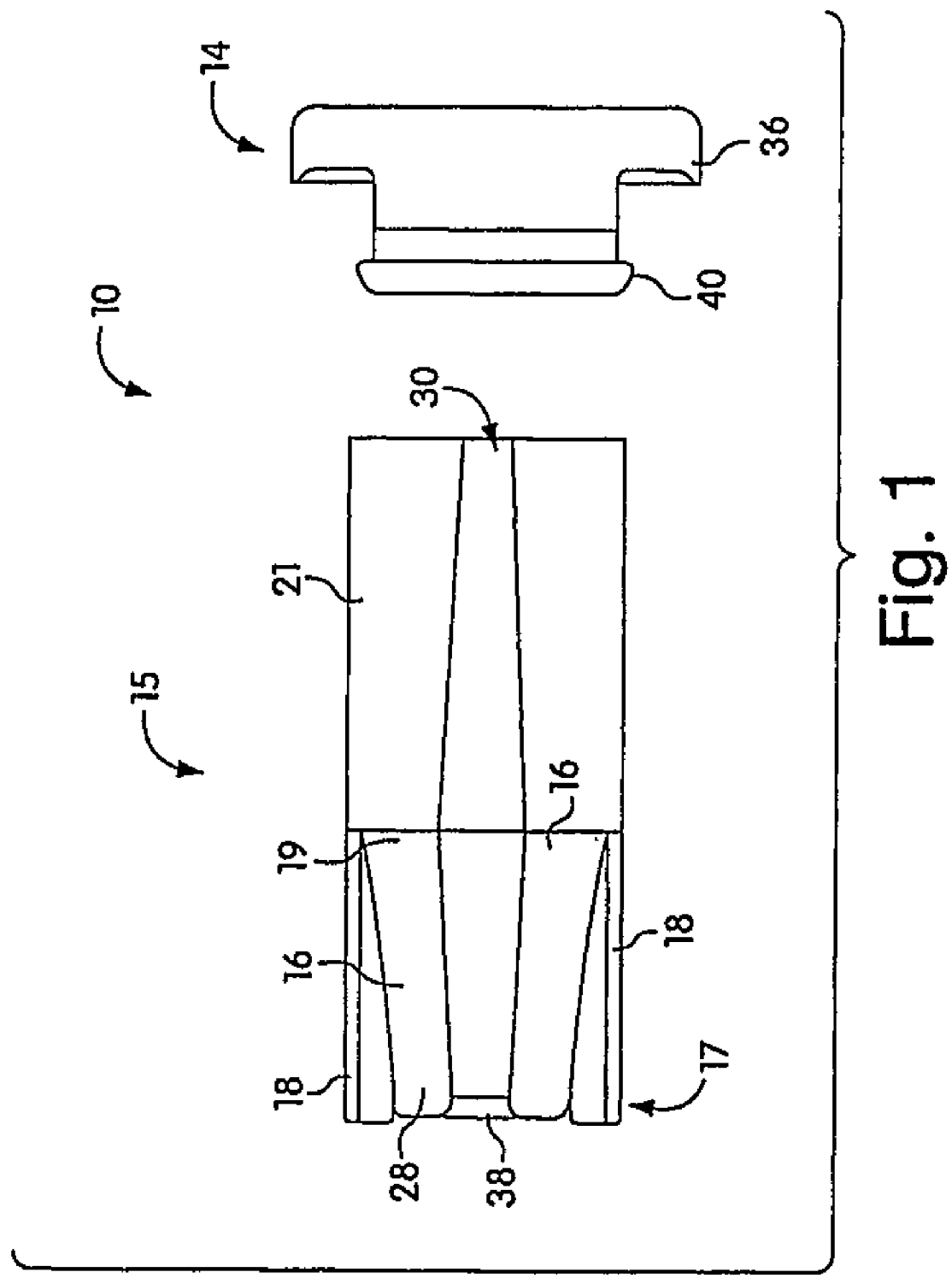

The invention claimed is:

1. An adapter for mounting an endoscopic accessory on the distal portion of an endoscope comprising:
   a centering sleeve mountable in the endoscopic accessory, the sleeve having a bore adapted to receive the distal end of an endoscope, the sleeve having a plurality of inwardly extending elements radially expandable in response to insertion of the distal portion of an endoscope into the sleeve whereby the sleeve may accommodate endoscopes of different diameter; and
   a collar engageable with the proximal end of the endoscopic accessory, the collar being mountable to the endoscope at a location proximally of the radially expandable elements of the centering sleeve.

2. A method for mounting an accessory on an endoscope comprising:
   providing an endoscopic accessory having a defined length and configured to fit over the end of an endoscope;
   inserting a first component of an adapter comprising radially expandable elements into a distal end of the accessory;
   inserting a second component of an adapter into a proximal end of the accessory;
   placing an accessory onto a distal end of an endoscope so that the accessory is supported along its length and retained on the endoscope shaft by the components of the adapter.

3. An endoscopic accessory mounting adapter kit comprising:
   a centering sleeve mountable in a distal end of an endoscopic accessory comprising a plurality of radially expandable elements;
   a plurality of collars mountable on the endoscope proximally of the sleeve and engageable with the proximal portion of the endoscopic accessory, each collar having a center hole of a diameter different than that of other collars in the kit.

4. The kit of claim 3 further comprising a gauge block endoscope measurement tool.

5. An adapter as defined in claim 1 further comprising:
   the centering sleeve having an abutment surface at its distal end, the abutment surface being adapted to engage a radially inwardly extending portion of the endoscope accessory to define the limit to which the sleeve can be inserted into the accessory.

6. An adapter as defined in claim 1 wherein the sleeve comprises a proximal portion and the radially expandable elements comprise circumferentially spaced, distally extending fingers extending from the proximal portion of the sleeve.

7. An adapter as defined in claim 6 wherein the distal ends of the radially expandable elements comprise radially inwardly extending lips adapted to abut the distal end of an endoscope inserted into the sleeve to limit the position of the sleeve on the endoscope.

8. An adapter as defined in claim 6 further comprising a longitudinally extending slot in the proximal portion of the sleeve to facilitate radial expansion of the proximal portion of the sleeve.

9. An adapter as defined in claim 1 wherein the collar has proximal and distal ends and comprises a radially extending flange at its proximal end, the flange having a diameter greater than that of the endoscopic accessory.

10. An adapter as defined in claim 9 wherein the endoscopic accessory includes a sealing ring mountable on the endoscope and wherein the collar includes a circumferential rib at its distal end, the rib being receivable in an annular groove formed in the inner circumferential surface of the sealing ring.

11. An adapter as defined in claim 9 further comprising an aperture formed in the proximal flange of the collar to enable control elements associated with an endoscopic accessory to extend proximally beyond the collar.

12. A kit as defined in claim 3 wherein the accessory has a handle by a cable connected to a portion of the accessory that is mountable on the distal end of an endoscope, each of the collars having an aperture to enable the cable to extend proximally of the collar.

13. An adapter as defined in claim 1 wherein the accessory includes a sealing ring mountable on an endoscope and wherein the collar is detachably connectable to the sealing ring.

14. An adapter kit as defined in claim 3 wherein each of the collars has an aperture receptive to a limited range of endoscope diameters and wherein the range of expansion of the radially expandable elements encompasses the range of endoscope diameters for which all of the collars in the kit are receptive.

* * * * *

UNITED STATES PATENT AND TRADEMARK OFFICE
CERTIFICATE OF CORRECTION

PATENT NO.       : 7,204,804 B2
APPLICATION NO.  : 10/656557
DATED            : April 17, 2007
INVENTOR(S)      : Zirps et al.

It is certified that error appears in the above-identified patent and that said Letters Patent is hereby corrected as shown below:

Sheets 1-7 and Title Page: replace with sheets 1-8 in formal form as shown in attached sheets.

Claim 2, column 7, line 30: replace "an accessory" with --the second component--.

Signed and Sealed this

Seventh Day of August, 2007

JON W. DUDAS
*Director of the United States Patent and Trademark Office*

United States Patent
Zirps et al.

(10) Patent No.: US 7,204,804 B2
(45) Date of Patent: Apr. 17, 2007

(54) ENDOSCOPIC ACCESSORY MOUNTING ADAPTOR

(75) Inventors: Christopher T. Zirps, Sharon, MA (US); Timothy R. Membrino, Acton, MA (US); Scott Reed, Monroe, CT (US); Eric Mears, South Bristol, ME (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/656,557

(22) Filed: Sep. 5, 2003

(65) Prior Publication Data
US 2004/0215058 A1 Oct. 28, 2004

Related U.S. Application Data

(60) Provisional application No. 60/408,750, filed on Sep. 6, 2002.

(51) Int. Cl.
*A61B 1/00* (2006.01)

(52) U.S. Cl. .............. 600/127; 600/129; 600/104
(58) Field of Classification Search ............ 600/127, 600/104, 129, 121, 123
See application file for complete search history.

(56) References Cited

U.S. PATENT DOCUMENTS

| | | | |
|---|---|---|---|
| 4,226,239 A | 10/1980 | Polk et al. |
| 4,230,116 A | 10/1980 | Watson |
| 4,735,194 A | 4/1988 | Stiegmann |
| 4,788,966 A | 12/1988 | Yoon |
| 5,201,908 A | 4/1993 | Jones |
| 5,259,366 A | 11/1993 | Reydel et al. |
| 5,275,151 A | 1/1994 | Shockey et al. |
| D344,334 S | 2/1994 | Dulebohn et al. |
| 5,325,746 A | 7/1994 | Anderson |
| 5,356,416 A | 10/1994 | Chu et al. |
| 5,382,254 A | 1/1995 | McGarry et al. |
| 5,383,875 A | 1/1995 | Bays et al. |
| 5,409,478 A | 4/1995 | Gerry et al. |
| 5,447,148 A | 9/1995 | Oneda |
| 5,470,328 A | 11/1995 | Furnish et al. |
| 5,493,256 A | 3/1996 | Furnish |
| 5,503,616 A | 4/1996 | Jones |
| 5,507,797 A | 4/1996 | Suzuki et al. |
| 5,569,268 A | 10/1996 | Hosoda |
| 5,601,568 A | 2/1997 | Chevillon et al. |

(Continued)

OTHER PUBLICATIONS

U.S. Appl. No. 10/656,083, filed Sep. 5, 2003, Zirps et al.

(Continued)

*Primary Examiner*—Beverly M. Flanagan
(74) *Attorney, Agent, or Firm*—Kirkpatrick & Lockhart Nicholson Graham LLP

(57) ABSTRACT

The present invention relates to a mounting adapter for releasably securing accessories, tools, or their medical instruments to the distal end of an endoscope. The adapter is compatible with endoscopic accessories that have a cylindrical mounting surface, which becomes positioned over a length of the distal end of an endoscope. The adaptor is preferably provided in two components to support both ends of a cylindrical accessory on the endoscope surface. The adapter is configured to hold the accessory on the endoscope shaft by frictional engagement and is configured to maintain the accessory concentric with the shaft along its length. The adapter also is configured to mount an accessory to a wide range of commercially available endoscope diameters.

14 Claims, 7 Drawing Sheets